United States Patent [19]

Rauhut et al.

[11] 4,366,079

[45] Dec. 28, 1982

[54] SULFONATED RUBRENE AND AQUEOUS CHEMILUMINESCENT COMPOSITIONS CONTAINING THE SAME

[75] Inventors: Michael M. Rauhut, Bridgewater; Arthur G. Mohan, Somerville, both of N.J.

[73] Assignee: American Cyanamid Company, Stamford, Conn.

[21] Appl. No.: 238,340

[22] Filed: Feb. 26, 1981

[51] Int. Cl.³ .................. C09K 11/06; C09K 11/14
[52] U.S. Cl. ................... 252/188.3 CL; 23/927; 260/505 C
[58] Field of Search ............ 252/188.3 CL; 23/927; 260/505 C, 507 R, 512 C, 501.21

[56] References Cited

U.S. PATENT DOCUMENTS

| | | | |
|---|---|---|---|
| 3,391,069 | 7/1968 | Rauhut | 252/188.3 CL |
| 3,470,103 | 9/1969 | Sheehan | 252/188.3 CL |
| 3,557,233 | 1/1971 | Zweig et al. | 252/188.3 CL |
| 3,630,941 | 12/1971 | Bergmark | 252/188.3 CL |
| 3,637,784 | 1/1972 | Sheehan | 252/188.3 CL |
| 4,053,430 | 10/1977 | Mohan | 252/188.3 CL |
| 4,226,738 | 10/1980 | Rauhut | 252/188.3 CL |
| 4,282,357 | 8/1981 | Tseng et al. | 544/85 |

FOREIGN PATENT DOCUMENTS 1067607  5/1967  United Kingdom ...... 252/188.3 CL

*Primary Examiner*—Irwin Gluck
*Attorney, Agent, or Firm*—Gordon L. Hart

[57] ABSTRACT

Water-soluble sulfonated rubrenes are used as fluorescer components in water-soluble chemiluminescent mixtures and particularly in combination with a water-soluble amide of oxalic acid which reacts with hydrogen peroxide to produce chemiluminescence.

12 Claims, No Drawings

SULFONATED RUBRENE AND AQUEOUS CHEMILUMINESCENT COMPOSITIONS CONTAINING THE SAME

The invention described herein was made in the performance of work supported by the Office of Naval Research (Contract No. N-00014-77-C-0634), and is subject to the provisions of ASPR 7-104.18, December, 1969, and ASPR 7-302.23(b) long form, August, 1977.

This invention is related to novel sulfonated rubrene compositions, and aqueous chemiluminescent compositions containing the same which are useful for the generation of visible chemiluminescent emission.

The art of generating light via chemical energy, that is, chemiluminescence, by the reaction of quaternary salts of N,N'-bis(morpholinoalkyl)-N,N'-bis(trifluoromethylsulfonyl)oxamides, and of N,N'-bis(pyridylalkyl)-N,N'-bis(trifluoromethylsulfonyl)oxamides, with hydrogen peroxide in an aqueous solvent in the presence of a fluorescer compound, is disclosed in co-pending U.S. patent application Ser. No. 122,621, filed on Feb. 19, 1980, now U.S. Pat. No. 4,282,357.

The generation of light by the reaction of an oxalic acid ester with a hydroperoxide in the presence of a fluorescer compound in aqueous systems has been disclosed in U.S. Pat. No. 4,053,430.

While efficient chemiluminescent reactions in non-aqueous solvents are known, only very low efficiencies are obtained in aqueous systems. There is a need, therefore, for aqueous chemiluminescent systems having improved efficiencies.

The present invention provides novel sulfonated rubrene represented by formula (I):

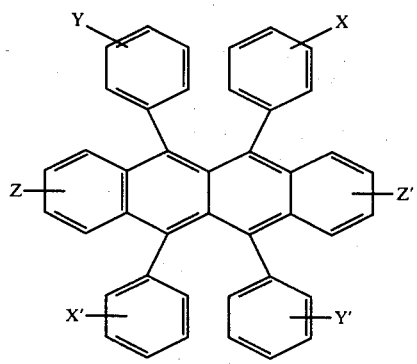

wherein X, Y, Z, X', Y', and Z' independently represent hydrogen, $C_1-C_6$ alkyl, chloro, fluoro, carboxy, $C_1-C_6$ alkoxy, hydroxy, $C_6-C_{12}$ aryloxy, and

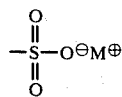

wherein $M^\oplus$ represent ammonium, $C_1-C_6$ alkylammonium, $C_1-C_6$ dialkylammonium, $C_1-C_6$ trialkylammonium, or an alkali metal ion, with the proviso that each sulfonated rubrene contains the substituent

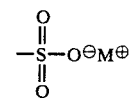

in an amount sufficient to produce water solubility to the extent of $1 \times 10^{-4}$ mole per liter, preferably about $1 \times 10^{-2}$ mole per liter, at ambient temperature.

When a fluorescer compound of formula (I) is mixed with an aqueous solution of a water-soluble amide of oxalic acid represented by formula (II):

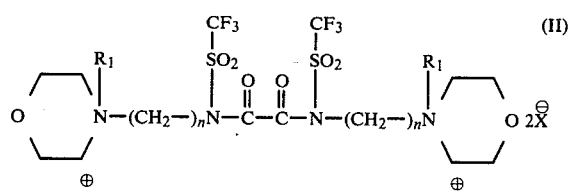

wherein $R_1$ is hydrogen, or $C_1-C_6$ alkyl, n is an integer from 2 to 6, and $X^-$ is an anion, and hydrogen peroxide, or a source of hydrogen peroxide, the mixture produces a chemiluminescent emission of superior efficiency, about 1.75% as contrasted with an efficiency of about 0.08% for aqueous systems containing the best water-soluble fluorescer described in the prior art.

Aqueous systems, containing a fluorescer of formule (I) and an oxamide of formula (II), are much more efficient than systems containing the same fluorescer with water-soluble esters of oxalic acid described in the prior art.

The fluorescer compounds, useful in the chemiluminescent compositions of this invention, may be defined broadly as water-soluble compounds of formula (I) which do not react with a hydrogen peroxide compound or the amide of oxalic acid on contact.

The fluorescers of formula (I) can be prepared by cyclizing an intermediate of formula (III) as

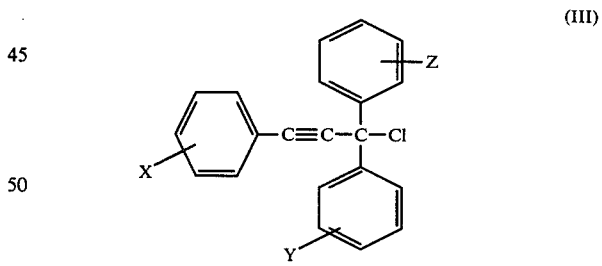

described by Wittig and Waldi (J. für praktische Chemie 160, 242 (1942), or by Rigandy and Capdevielle [Tetrahedron 33, 767 (1977)]. Alternatively, the substituents may be introduced directly on the rubrune, before or after sulfonation, by appropriate reactions such as halogenation, alkylation, and the like. The critical factor is that sufficient $-SO_3^\ominus M^\oplus$ substituents be present to provide the required water-solubility.

The oxamides of formula (II) may be obtained by reacting two moles of a sulfonamide with one mole of oxalyl chloride in an anhydrous organic solvent, such as tetrahydrofuran, under an inert atmosphere. The oxamide may be quaternized with an appropriate alkylating agent yielding the corresponding trifluoromethanesulfonate, methanesulfonate, p-toluene sulfonate, methosulfate, or halide salt.

Typical oxamides of formula (II), which may be employed, are those compounds wherein the anion is selected from chloride, bromide, fluoride, methanesulfonate, methosulfate, trifluoromethanesulfonate, tetrafluoroborate, and the like.

Illustrative examples of compounds of formula (II) within the purview of this invention include the dihydrochlorides, dihydrobromides, dihydrofluorides, di(-trifluoromethane)sulfonates, dimethanesulfonates, dimethosulfates, and ditetrafluoroborates of the following compounds:

N,N'-bis(2-morpholinoethyl)-N,N'-bis(trifluoromethylsulfonyl)oxamide,
N,N'-bis(3-morpholinopropyl)-N,N'-bis(trifluoromethylsulfonyl)oxamide,
N,N'-bis(6-morpholinohexyl)-N,N'-bis(trifluoromethylsulfonyl)oxamide, and the like.

The preferred compounds of formula (II) do not react with the fluorescer compound on contact, and have an anion which does not react with a hydrogen peroxide compound.

The term "hydrogen peroxide compound," as used herein, means hydrogen peroxide or a compound that produces hydrogen peroxide by reaction or decomposition, such as sodium perborate, potassium perborate, sodium carbonate peroxyhydrate, histidine perhydrate, and the like.

The molar concentrations (moles per liter of solution) of the major components of the novel compositions, described herein, may vary considerably. It is only necessary that the components be present in sufficient concentration to obtain chemiluminescence. The molar concentration of the oxamide normally is in the range of $10^{-3}$ to 5, preferably about $10^{-2}$ to 1.0. The molar concentration of the fluorescer compound used is from about $10^{-5}$ to $10^{-1}$, preferably $10^{-4}$ to $10^{-2}$. The molar concentration of the hydrogen peroxide compound used is from about $10^{-3}$ to 10.0, preferably $10^{-1}$ to 4.0. The optimum mole ratio of hydrogen peroxide compound to oxamide used ranges from about 0.5 to 10.0.

The ingredients of the chemiluminescent compositions of this invention are kept separated until chemiluminescence is desired, when they may be admixed in a single step or in a series of steps. The order of admixing of the ingredients is usually not critical. The hydrogen peroxide compound and fluorescer compound may be dissolved in water and the oxamide added thereto to initiate chemiluminescence. The oxamide may be added as a solid or in a suitable diluent. Alternatively, the oxamide and the fluorescer compound may be dissolved in water and the hydrogen peroxide compound added thereto to initiate chemiluminescence. Preferably, a solution of the hydrogen peroxide compound in water is added to a solid mixture of oxamide and fluorescer to initiate chemiluminescence.

The intensity of the chemiluminescence is relatively independent of the pH of the reaction medium. Variation of the pH from about 3 to 8 has no discernible effect on the intensity of light emitted in the visible range.

Superior intensity of chemiluminescence is obtained when the final mixture producing the luminescence is maintained at a temperature from about $-10°$ to $50°$ C., preferably from about $15°$ to $40°$ C.

The invention is described in more detail by the following examples in which concentrations in moles per liter are indicated by the letter "M."

EXAMPLE 1

Preparation of Sulfonated Rubrene

A solution of rubrene (2.5 grams; 0.0047 mole) in dichloromethane (100 mls) is cooled in an ice-water bath and 30 mls of a solution of dichloromethane containing sulfur trioxide (1.98 grams; 0.025 mole) is added to the stirred mixture over a period of one hour. The reaction mixture is stirred for an additional hour without cooling and then drowned in ice water. The pH of the resulting mixture is adjusted to 8 by adding sodium bicarbonate and the alkaline mixture is heated to remove the dichloromethane. The resulting solution is filtered and the filtrate is heated under vacuum to remove the solvent. The resulting solid residue (6.5 grams) is extracted with ethanol-3A in a Soxhlet extractor for three hours and the resulting extract is heated under vacuum to obtain 1.3 grams of solid. The latter is dissolved in 20 mls of ethanol 3A, cooled, and filtered to remove 0.22 gram of insoluble material. Concentration of the filtrate gives 1.0 gram of solid. The latter is dissolved in acetone containing some methanol to effect dissolution and put on a silica gel column on a Waters 500A Preparative Liquid Chromatograph. The column is eluted with acetone and four liters of eluant are separated. The column is then eluted with methanol and four liters of methanol eluant are collected. Concentration of the methanol eluant under vacuum gives a red solid which is dissolved in water and filtered to remove some insoluble material. Concentration of the aqueous filtrate gives 0.37 gram of product.

EXAMPLE 2

Preparation of 4,4'-{Oxalyl bis[[(trifluoromethyl)sulfonyl]imino]ethylene} Bis(4-methylmorpholinium trifluoromethanesulfonate Oxalyl chloride (11.10 grams; 0.076 mole) is added dropwise to a solution of N-(2-morpholinoethyl)trifluoromethanesulfonamide (37.72 grams; 0.152 mole) and triethylamine (15.39 grams; 0.153 mole) in dry tetrahydrofuran (400 mls) at 0° C. under a nitrogen atmosphere over a period of 90 minutes. After the addition is completed, the mixture is stirred at room temperature for 4 hours and then filtered. The filtrate is concentrated to remove tetrahydrofuran and obtain 34.36 grams of the crude product. Recrystallization of the crude product from petroleum ether gives N,N'-bis(2-morpholinoethyl)-N,N'-bis(trifluoromethylsulfonyl)oxamide, m.p. 62°–64° C.

Methyl trifluoromethanesulfonate (4.35 grams; 0.027 mole) is added portionwise to a solution of the N,N'-bis(2-morpholinoethyl)-N,N'-bis(trifluoromethylsulfonyl)oxamide (3.0 grams; 0.0052 mole) in methylene chloride (30 mls) at 0° C. under anitrogen atmosphere. After the addition is completed, the mixture is stirred at room temperature for an additional 2 hours. The white solid precipitate is then separated by filtration and washed several times with methylene chloride. After drying under vacuum, the product melts at 121°–125° C.

EXAMPLES 3–5

Quantitative Determination of Chemiluminescence

Aqueous hydrogen peroxide (2.8 mls; 1.75 M), containing sodium salicylate (0.0012 M) is added to a cuvette containing a mixture of the compound of Example 1 and the compound of Example 2 (0.1 gram) to provide 0.0404 M of the compound of Example 2, and the weight concentrations of the fluorescer compound of Example 1 indicated in Table I.

The emission intensity is then measured at 575 nm by means of a spectroradiometer-luminometer similar to that described by Roberts and Hirt [Appl. Spectrosc., 21, 250 (1967)] modified with a Jarrell-Ash Model 82-410 grating monochromator and an RCA C31034 photomultiplier with a gallium arsenide photocathode operated at 1300 V with dry ice cooling. Raw data are recorded digitally on a Hewlett-Packard 5150 A thermal printer. Spectral response is corrected by calibration against a standard tungsten lamp. Absolute light intensities are obtained by deriving calibration constants based on the accepted fluorescence quantum yield (0.55) for quinine sulfate, as reported by Melkuish [N.Z. Sci. Tech., B, 37, 142, (1955)] in 0.1 N $H_2SO_4$, and by ferrioxalate actinometry [Hatchard et al., Proc. R. Soc. London, Ser. A, 235, 518 (1956)] of the exciting light. Chemiluminescence quantum yields in einsteins per mole of compound under test are calculated by monitoring the intensity decay at a single wavelength and calculating the intensity at each time interval in einsteins per second from the chemiluminescence spectrum. Chemiluminescence spectra are then corrected for intensity decay. The total area under the decay curve is calculated by using a combination of a Simpson's rule integration and an exponential extrapolation to infinite time as described by Roberts and Hirt. Data are processed by a Digital Equipment Corp. PDP-1140 computer. The results obtained are shown in Table I.

TABLE I

| Example | Fluorescer (g/l) | Percent Quantum Yield[a] | Light Capacity[b] | Time₃[c] |
|---|---|---|---|---|
| 3 | 7.5 | 1.97% | 15.9 | 12 |
| 4 | 7.5 | 1.52 | 12.3 | 11 |
| 5 | 0.75 | 0.14 | 1.4 | 14 |

[a] Percent Quantum Yield = einsteins per mole of reactant × $10^2$
[b] Light Capacity = lumen-hours per liter of emitting solution
[c] Time₃ = minutes required for 75% of the light to be emitted at the emission peak of the fluorescer.

EXAMPLES 6 AND 7

In the manner described in Examples 3–5, aqueous hydrogen peroxide (2.8 mls; 1.75 M), containing sodium salicylate (0.0012 M), is added to two cuvettes, each containing an amount of the compound of Example 2 to provide a concentration of 0.0404 M, one cuvette containing the trisodium salt of 8-hydroxy-1,3,6-pyrenetrisulfonic acid (0.01 gram), and the other containing disodium 9,10-diphenylanthracene-2,6-disulfonate (0.01 gram) as fluorescers. Each fluorescer is present in the reaction mixture at a concentration of 0.0068 M. The results obtained are shown in Table II.

TABLE II

| Example | Percent Quantum Yield | Light Capacity | Time₃ |
|---|---|---|---|
| 6 | 0.0074 | 0.084 | 20 |
| 7 | 0.08 | 0.473 | 24 |

Comparison of the results obtained above with the results obtained in Examples 3 and 4 shows that the mean quantum yield of Examples 3 and 4 of 1.75% is more than twenty times higher than that obtained with disodium 9,10-diphenylanthracene-2,6-disulfonate, the most efficient prior art fluorescer with the produce of Example 2.

EXAMPLE 8

The procedure of Examples 3 and 4 is followed in every detail except that the bis tetramethylammonium salt of bis(2,3,6-trichloro-4-sulfophenyl)oxalate is used at a concentration of 0.05 M, instead of the product of Example 2. The results obtained are shown below.

TABLE III

| Quantum Yield | Light Capacity | Time₃ |
|---|---|---|
| 0.02% | 0.22 | 0.1 |

Comparison of the results obtained above with the results obtained in Examples 3 and 4 shows that the average quantum yield of Examples 3 and 4 is about 87.5 times that obtained above. This shows the superiority of the combination of the products of Examples 1 and 2 over the combination of the product of Example 1 and a water-soluble ester of oxalic acid.

We claim:

1. A sulfonated rubrene represented by the formula (I):

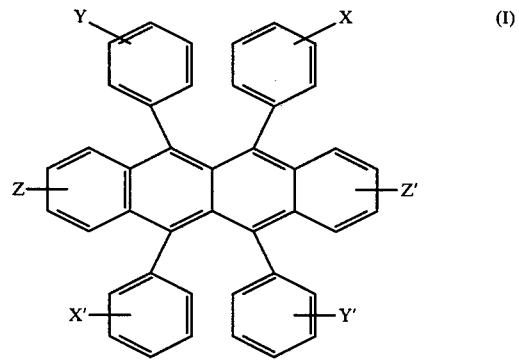

wherein each of the X, Y, Z, X', Y', and Z' substituents independently represents a member selected from the group consisting of hydrogen, $C_1$–$C_6$ alkyl, chloro, fluoro, carboxy, $C_1$–$C_6$ alkoxy, hydroxy, $C_6$–$C_{12}$ aryloxy, and

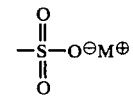

wherein M⊕ represents a member selected from the group consisting of ammonium, $C_1$–$C_6$ alkylammonium, $C_1$–$C_6$ dialkylammonium, $C_1$–$C_6$ trialkylammonium, and alkali metal ions, and wherein the defined sulfonated rubrene contains the substituent

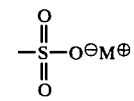

in an amount at least sufficient to produce water-solubility of the sulfonated rubrene to the extent of $1 \times 10^{-4}$ moles per liter at ambient temperature.

2. The composition of claim 1 wherein three of the substituents are —SO$_3^{\ominus}$ Na$^{\oplus}$ and the others are hydrogen.

3. The composition of claim 1 wherein four of the substituents are —SO$_3^{\ominus}$ Na$^{\oplus}$ and the others are hydrogen.

4. A composition useful for generating chemiluminescent emission comprising an aqueous solution of a sulfonated rubrene defined by claim 1, and a water-soluble amide of oxalic acid represented by formula (II):

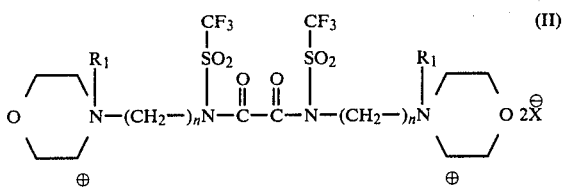

wherein R$_1$ represents hydrogen, or C$_1$-C$_6$ alkyl, n is an integer from 2 to 6, and X$^{\ominus}$ is an anion, in proportions capable of producing chemiluminescence on contact with a hydrogen peroxide compound.

5. A composition according to claim 4 wherein X$^{\ominus}$ is an anion selected from chloride, bromide, fluoride, methanesulfonate, methosulfate, trifluoromethanesulfonate, or tetrafluoroborate.

6. A composition, as defined in claim 5, wherein the amide is 4,4'-{Oxalyl bis[[(trifluoromethyl)sulfonyl]-iminio]ethylene}bis(4-methylmorpholinium trifluoromethanesulfonate).

7. A composition, as defined by claim 5, wherein the amide is 4,4'-{Oxalyl bis[[(trifluoromethyl)sulfonyl]-imino]ethylene}bis(morpholinium chloride).

8. A composition, as defined in claim 5, wherein the amide is 4,4'-{Oxalyl bis[[(trifluoromethyl)sulfonyl]-imino]ethylene}bis(4-methylmorphloinium tetrafluoroborate).

9. A composition defined in claim 5 wherein the amide is 4,4'-{Oxalyl bis[[(trifluoromethyl)sulfonyl]-]imino]trimethylene}bis(morpholinium chloride).

10. A composition defined in claim 5 wherein the amide is 4,4'-{Oxalyl bis[[(trifluoromethyl)sulfonyl]-]imino]trimethylene}bis(4-methylmorpholinium trifluoromethanesulfonate).

11. A process for generating chemiluminescence comprising adding an effective amount of an aqueous solution of hydrogen peroxide, or a source of hydrogen peroxide, into an aqueous solution of a sulfonated rubrene defined by claim 1.

12. A process for generating chemiluminescence comprising adding an effective amount of a water-soluble amide of oxalic acid into an aqueous solution of hydrogen peroxide or a source of hydrogen peroxide and a water-soluble sulfonated rubrene defined by claim 1.

* * * * *